United States Patent [19]

Moriya et al.

[11] Patent Number: 5,342,778
[45] Date of Patent: Aug. 30, 1994

[54] MICROORGANISM BELONGING TO THE GENUS FLAVOBACTERIUM DESIGNATED FERM BP-4010

[75] Inventors: Kazuhito Moriya; Koki Horikoshi, both of Tokyo, Japan

[73] Assignees: Japan Marine Science and Technology Center, Yokosuka; Hokkaido Sugar Co., Ltd., Tokyo, both of Japan; a part interest

[21] Appl. No.: 950,586

[22] Filed: Sep. 25, 1992

[30] Foreign Application Priority Data

Sep. 30, 1991 [JP] Japan ................................ 3-252195
Sep. 30, 1991 [JP] Japan ................................ 3-252196

[51] Int. Cl.$^5$ .......................... C12N 1/26; C12N 1/00; C12N 1/20; D06M 16/00
[52] U.S. Cl. ................................ 435/252.1; 435/248; 435/262.5; 435/264; 435/850
[58] Field of Search ................. 435/252.1, 248, 262.5, 435/264, 850

[56] References Cited

U.S. PATENT DOCUMENTS

| | | | |
|---|---|---|---|
| 3,510,403 | 5/1970 | Laine et al. | 195/82 |
| 3,642,577 | 2/1972 | Gorring | 195/28 R |
| 3,898,959 | 8/1975 | Chen et al. | 195/28 R |
| 4,410,625 | 10/1983 | Cadmus | 435/42 |
| 4,981,800 | 1/1991 | Inoue et al. | 435/248 |

FOREIGN PATENT DOCUMENTS

| | | |
|---|---|---|
| 0161511 | 11/1985 | European Pat. Off. . |
| 0281523 | 9/1988 | European Pat. Off. . |
| 0315949 | 5/1989 | European Pat. Off. . |
| 2084608 | 4/1982 | France .................. 435/248 |
| 2069983 | 3/1987 | Japan .................... 435/248 |

OTHER PUBLICATIONS

Biosis Previews, Biosis, AN-75056578, S. Nagata, "Degradation of Aliphatic and Aromatic Hydro Carbons by Marine Bacteria", 1982.

Biosis Previews, Biosis, AN-80103697, T. Higashihara, et al., "Generic Composition and Degradation Activity Hydrocarbon-Degrading Bacterial Isolated Form the Open-Sea", 1985.

Primary Examiner—Douglas W. Robinson
Assistant Examiner—Deborah K. Ware
Attorney, Agent, or Firm—Oblon, Spivak, McClelland, Maier & Neustadt

[57] ABSTRACT

A microorganism belonging to the genus Flavobacterium possessing the capacity to decompose hydrocarbons, tolerance to sulfurous acids, tolerance to salinity, tolerance to organic solvents, and tolerance to pressure. The microorganism is a strain of the genus Flavobacterium DS-711 (FERM BP-4010).

2 Claims, No Drawings

MICROORGANISM BELONGING TO THE GENUS FLAVOBACTERIUM DESIGNATED FERM BP-4010

BACKGROUND OF THE INVENTION

1. Field of the Invention

The present invention relates to a novel microorganism belonging to the genus Flavobacterium, a hydrocarbon emulsifier and solubilizer and a separation method for organic-solvent tolerant microorganisms. To explain in greater detail, the present invention relates to a novel microorganism belonging to the genus Flavobacterium having an ability to decompose hydrocarbons, tolerance to sulfurous acids, tolerance to salinity, tolerance to organic solvents, and tolerance to pressure and a hydrocarbon emulsifier and solubilizer produced by the microorganism.

2. Prior Art

Recently, marine pollution resulting from oil products such as kerosene, heavy oil, and the like, has become increasingly frequent, and has created many problems. As a method of solving this type of problem, the development of a microorganism which can efficiently and easily decompose all the hydrocarbons contained in oil pollution at sea has been desired; however, a microorganism having sufficient capacity has not yet been discovered. Examples of microorganisms which convert and decompose simple hydrocarbons contained in oil have included microorganisms belonging to the genus bacillus, the genus Acinetobacter, the genus Pseudomonas, the genus Moraxella, the genus Arcadia, and the genus Candida, which have been isolated from earth or sea water; however, these are not satisfactory in that they do not possess the tolerance to salinity, tolerance to organic solvents, and the like, which are necessary for the decomposition of oil pollution and the like at sea.

In order to decompose oil pollution and the like floating at sea, it is necessary that a microorganism be able to efficiently decompose oil products such as kerosene and heavy oil and the like, and that such a microorganism possess tolerance to toxicity resulting from hexane, benzene, toluene, xylene which are the organic solvents contained in these oil products, tolerance to salt which is present in large concentrations in sea water, and furthermore, tolerance to pressure. A microorganism possessing all of these qualities has not yet been discovered.

On the other hand, a substance which can efficiently and easily emulsify and solubilize all hydrocarbons contained in oil pollution floating at sea has been sought as a means to solve such problems; however, the substance possessing such properties in sufficient amounts has not yet been discovered. Many scientists have conducted research in the field of emulsifying and solubilizing substances which are produced by microorganisms, and it has been discovered that a number of types of microorganisms belonging to the genus Bacillus, the genus Acinetobacter, the genus Pseudomonas, the genus Moraxela, and the genus Candida and the like produce substances which possess the ability to emulsify and solubilize oil products. However, even if such substances produced by microorganisms are used, it is not possible to efficiently emulsify and solubilize oil; for example, the emulsifying and solubilizing substances produced by the genus Acinetobacter are unstable, losing their effect in a short time period and the like.

Conventionally, in order to separate a microorganism possessing such tolerance, and particularly, tolerance to organic solvents, a method was adopted in which a sample was added to a culture medium containing organic solvents and cultured, and microorganisms growing in this culture medium were isolated. However, this method was not merely time-consuming, but also had extremely low separation efficiency.

SUMMARY OF THE INVENTION

Accordingly, an object of the present invention is to provide a microorganism which possesses a superior ability to decompose hydrocarbons, along with superior tolerance to salinity, organic solvents, and the like.

A further object of the present invention is to provide a substance produced by microorganisms which is able to effectively emulsify and solubilize hydrocarbons in environments such as sea water.

A still further object of the present invention is to provide a method by which microorganisms possessing higher tolerance to organic solvents may be separated efficiently and in a short period of time.

DETAILED DESCRIPTION OF THE INVENTION

At the Marine Science Technology Center, the manned submarines Shinkai 2000 and Shinkai 6500 have been developed which are capable of collecting mud at a maximal undersea depth of 6500 meters. The present inventors have conducted research in order to isolate from deep-sea mud collected by means of these manned submarines, microorganisms which fulfill the above conditions; and as a result; have discovered that a novel microorganism belonging to the genus Flavobacterium meets the above conditions and the present invention was arrived at on the basis of this discovery.

The present invention provides a novel microorganism belonging to the genus Flavobacterium which possesses such ability to decompose hydrocarbons, and in addition possesses tolerance to sulfurous acids, tolerance to salinity, tolerance to organic solvents, and tolerance to pressure. An example of such a novel microorganism is the genus Flavobacterium strain DS-711.

The present inventors have also discovered that by using an emulsifying and solubilizing substance produced the novel microorganism belonging to the genus Flavobacterium, it is possible to efficiently emulsify and solubilize oil products such as kerosene, heavy oil, and the like, even in environments such as that of sea water, and on the basis of this discovery, have arrived at the present invention.

The present invention provides an emulsifier and solubilizer having as active ingredients thereof water soluble and acetone insoluble fractions obtained by the culturing in a culture medium containing hydrocarbons of the DS-711 strain of the genus Flavobacterium, which possesses an ability to decompose hydrocarbons, tolerance to salinity, tolerance to organic solvents, and tolerance to pressure.

The present invention further provides a separation method for organic-solvent tolerant microorganisms wherein a sample is mixed with water and organic solvents, culturing with shaking is conducted, the culture mixture is left to stand, separation into a water phase and an organic solvent phase is conducted, an appropriate amount of the organic solvent phase is added to a culture medium and cultured, and microorganisms which grow therein are isolated.

The isolation of the DS-711 strain of the genus Flavobacterium is accomplished according to the following method.

That is to say, mud previously collected from the ocean floor is processed with hexane of a 2% concentration, and after this processing, it is processed with 50% kerosene. The lipophilic cells which move to the kerosene layer are cultured in an agar culture medium consisting of a basis culture medium comprising 0.1% of proteose peptone No. 3, 0.05% of phytone, 0.1% of calcium chloride, 0.005% of sodium sulfite, and 0.01% of magnesium chloride (this culture medium was termed the "Moriya" culture medium, and is referred to hereinafter as "M-culture medium") to which was added 0.1% kerosene, one mole of sodium chloride, and 1.5% of agar and a number of colony strains are thus obtained. These strains are further cultured in M-culture medium containing 1.0% of kerosene and 1 mole of sodium chloride, and the cells exhibiting the most superior growth after culturing are selected. This is the DS-711 strain of the genus Flavobacterium which is the novel microorganism of the present invention. This DS-711 strain was isolated from mud taken from the ocean floor of Suruga bay at a depth of 1945 m; it was deposited on Aug. 27, 1991 at Ministry of International Trade and Industry, Agency of Industrial Science and Technology, Fermentation Research Institute, Japan under the accession number of FERM BP-4010 (hereinafter termed the "DS-711" strain).

Next, further explanation will be made of the mycological properties of the microorganism of the present invention and of the culturing method thereof.

The microorganism of the present invention includes, in addition to the DS-711 strain, naturally occurring and artificial variations thereof.

The DS-711 strain possesses the following mycological characteristics.

(1) Morphology

The microorganism is a short bacillus with a size of (0.5–0.7)×(1.0–2.0) microns. It does not form spores. It is capable of movement and possesses peripheral flagella. Gram's stain is negative.

(2) Physiological characteristics
1. Reduction of nitrates: negative
2. Starch hydrolysis: negative
3. Formation of pigments: present (colony: orange-pink)
4. Oxidase: positive
5. Catalase: positive
6. Growth range:
   pH 5.0–9.5 (optimally 7.0–8.0)
   12°–42° C. (optimally 35°–37° C.)
7. Oxygen requirement: absolutely aerobic
8. O-F test: oxidized
9. Production of acids or gases from saccharides: not present (3) Other characteristics
1. Tolerance to sodium chloride: growth at a sodium chloride density of 3 moles
2. Amount of GC contained in DNA: 67.4 mol %
3. Phosphatase: positive
4. Gelatin hydrolysis: negative
5. Casein hydrolysis: positive
6. Tween 20 hydrolysis: positive
7. Tween 80 hydrolysis: positive Based on the above mycological characteristics, this novel microorganism was judged to belong to the genus Flavobacterium according to the classification methods of volume 8 of the Bergey's Manual of Determinative Bacteriology, and was designated the DS-711 strain of the genus Flavobacterium.

The emulsifier and solubilizer of the present invention can be produced by means of the DS-711 strain according to the following method.

1 L of M-culture medium containing 5% sodium chloride is placed in a 5 L ribbed neck conical flask, and the DS-711 strain is inoculated to the culture medium. After the inoculation, 1 mL of kerosene is layered thereon, and culturing with agitation is conducted at a rotational speed of approximately 100 rpm for a period of 5 days at a temperature of 30° C. After culturing, in order to remove the cells which have grown, centrifugal separation is carried out and the clear upper liquid is obtained. This clear liquid is refrigerated at a temperature of 4° C., 3 L of acetone which has been refrigerated in advance is added thereto, this is agitated and mixed, then left to stand for 2 to 3 days. After this, the precipitate in the lower portion thereof is recovered by means of centrifugal separation. This recovered material is the emulsifier and solubilizer of the present invention.

Hereinbelow, the separation method for organic-solvent tolerant microorganism of the present invention will be explained in detail.

In the method of the present invention, it is preferable that the shaking culturing be conducted for a period of 1–7 days and at a temperature of 4°–30° C. The water used in the present invention is not particularly restricted; for example, it is acceptable to use deionized water, distilled water, sea water, artificial sea water, or the like. The pH of the water used should preferably be in a range of 4–9, more preferably in a range of 5–8, and most preferably should be close to neutral. The volume ratio of the water and organic solvent which are mixed with the sample should preferably be in a range of 1:9–9:1; and furthermore, 1–10 volume parts (weight parts) of the sample should preferably be added with respect to the total amount (100 volume parts) of the water and organic solvent.

Examples of the culture medium used for culturing appropriate amounts of the separated organic solvent phase include, for example, an agar culture medium.

The culturing of the organic solvent phase should preferably be carried out under conditions in which organic-solvent tolerant microorganisms will grow; for example, for a period of 1–10 days at a temperature of 20°–40° C., and preferably at 30° C.

The organic solvent used in the method of the present invention is used to separate a microorganism having tolerance to organic solvents; examples thereof include hydrocarbons which are typically in a liquid state at normal temperatures, and particularly aromatic hydrocarbons, aliphatic hydrocarbons, and alicyclic hydrocarbons. Examples of aromatic hydrocarbons include those having from 6 to 8 carbon atoms, for example, benzene, toluene, xylene, and the like; furthermore, examples of aliphatic hydrocarbons include those having from 5 to 16 carbon atoms, for example, pentane, hexane, heptane, octane, and the like; and in addition, examples of alicyclic hydrocarbons include those having from 5 to 8 carbon atoms, for example, cyclopentane, cyclohexane, cycloheptane, cyclooctane, and the like. Furthermore, examples of mixtures of these organic solvents include, for example, thinner, petroleum benzine, and the like.

Evaluation of an organic-solvent tolerant microorganism isolated in this manner may be conducted in the following manner.

Preculturing: 5 ml of a liquid culture medium is added to a test tube, and this is sterilized for a period of 20 minutes in an autoclave at a temperature of 120° C. Using a platinum loop, the isolated microorganism is inoculated to the sterilized culture medium, shaking culturing is conducted for 1 day at a temperature of 35° C., and a suspension of the microorganism thus precultured is prepared.

Evaluation Method: 5 ml of a liquid culture medium is added to a test tube, and this is sterilized in accordance with the above conditions. 100 microliters of the suspension of the above microorganism is inoculated to the sterilized culture medium, a further 50 microliters of organic solvent is added, a silicone rubber cap is attached, and shaking culturing is conducted for a period of 3 days at a temperature of 30° C. After shaking, microorganisms for which an increase in the absorbancy of the culture medium at a wavelength of 660 nm could be recognized in comparison with a control to which the microorganism is not inoculated are judged to be organic-solvent tolerant microorganisms.

The microorganism of the present invention exhibits superior decomposition activity with respect to hydrocarbons. Furthermore, the microorganism exhibits tolerance with respect to sulfurous acids, salinity, and various organic solvents including hexane, which are generally toxic with respect to microorganisms, so that it is capable of effectively decomposing oil pollution products such as kerosene or heavy oil floating at sea. Furthermore, the microorganism is not limited to the decomposition of oil products at sea, but rather may be used in various other environments in order to effectively decompose organic solvent pollution.

The hydrocarbon emulsifier and solubilizer produced by the DS-711 strain of the present invention is capable of effectively emulsifying and solubilizing hydrocarbons, and maintains this ability even in sea water. Accordingly, the hydrocarbon emulsifier and solubilizer of the present invention is capable of effectively emulsifying and solubilizing polluting oil products such as kerosene, heavy oil, or the like, floating at sea. Furthermore, the use thereof is not limited to the emulsification or solubilization of oil products at sea; rather, it is capable of effectively emulsifying and solubilizing various polluting organic solvents in various other environments.

In accordance with the separation method of the present invention, it is possible to efficiently separate a microorganism which has superior tolerance to organic solvents from a sample in a short period of time.

EXAMPLES

Hereinbelow, the present invention will be explained in greater detail based on examples.

EXAMPLE 1

Acquisition procedure of the DS-711 strain 100 microliters of n-hexane were added to 5 ml of silt deposit suspended in sea water taken from the deep-sea floor, and this was gently shaken for 1 week at a temperature of 4° C. After this shaking was completed, a further 5 ml of kerosene was layered thereon, and this was again vigorously shaken at room temperature for a period of 2 days and cultivation was thus carried out. After cultivation, the cultured material was left standing for a period of 30 minutes, the kerosene layer and the water layer were separated, 50 microliters of the kerosene layer was applied to M-agar culture medium containing 1 mole of sodium chloride and 1.5% agar, and this was left standing for a period of 5 days at a temperature of 20°–30° C., and culturing conducted. After culturing, the numerous colonies which developed were isolated, these were each individually placed in M-culture medium containing 1% of kerosene and 1 mole of sodium chloride, and culturing was conducted while shaking for a period of 2 days at a temperature of 30° C. After the conclusion of these operations, the colony which had exhibited the best growth among all the colonies was identified; and this was the DS-711 strain of the present invention.

EXAMPLE 2

Kerosene decomposition by means of DS-711

Preculturing of the microorganism: 10 ml of M-culture medium containing 1 mole of sodium chloride was placed in a large test tube, a silicone rubber plug was affixed, and this was sterilized. After sterilization, the DS-711 strain bacilli were scraped off using a platinum wire loop from a culturing slanted surface, were applied to a culture medium, and culturing while being vigorously shaken was conducted for 24 hours at a temperature of 37° C.

Kerosene decomposition tests: 100 ml of M-culture medium containing 1 mole of sodium chloride was placed in a 500 ml ribbed conical flask, and after sterilization, 1 ml of a suspended solution of the above-described culture material was placed thereon. After placement, 10 ml of kerosene was layered on top, and this was cultured while being shaken for a period of 1 week at a temperature of 35° C. After culturing, centrifugal separation was carried out, the biomass was removed, the clear upper liquid thereof was transferred to a separatory funnel, the remaining kerosene phase and aqueous phase of the culture medium were separated, 50 ml of benzene containing 0.1 g of cotacosane was added to each, and the hydrocarbons were extracted. After the extraction, sodium sulfate anhydride was added to the benzene, and after dehydration, this was concentrated, and individual straight chain hydrocarbons having 6 to 16 carbon atoms were analyzed by means of gas chromatography. The results are shown in Table 1 below.

Conditions of gas chromatography: Gas Chromatography: Shimadzu GC-14A,

Detector: single-flame ionization detector, Column: glass column 2.1 m by 3.2 m/m), Carrier: silicone 10% OV-101, 60/80 mesh chromosobe WAW-DMCS, Carrier gas: $N_2$ (40–50 ml/min), Temperature: 35°–300° C. (programmed speed 10° C./min)

TABLE 1

Decomposition of hydrocarbons contained in kerosene

| Hydrocarbon | Hydrocarbon amount (mg) | Control group hydrocarbons (no inoculation) | | Experimental group hydrocarbons | |
|---|---|---|---|---|---|
| | | kerosene phase | aqueous phase | kerosene phase | aqueous phase |
| n-hexane | 0.8 | ND | ND | ND | ND |
| n-heptane | 56 | 34 | ND | ND | 0.02 |
| n-octane | 72 | 39 | ND | 7 | ND |
| n-nonane | 236 | 190 | ND | 34 | ND |
| n-decane | 312 | 245 | ND | 70 | ND |
| n-undecane | 320 | 270 | 0.04 | 85 | 1.4 |
| n-dodecane | 704 | 652 | 0.08 | 150 | 1.7 |
| n-tridecane | 596 | 501 | 0.09 | 134 | 2.4 |
| n-tetradecane | 364 | 332 | 0.09 | 78 | 1.7 |
| n-pentadecane | 212 | 188 | 0.07 | 12 | 1.3 |
| n-hexadecane | 48 | 39 | 0.02 | 7 | 0.6 |

ND: nondetectable

The total concentration of the hydrocarbons having 6 to 16 carbon atoms contained in the kerosene supplied to the test above corresponds to 29.2% of contained kerosene.

EXAMPLE 3

Decomposition by means of DS-711 strain of hydrocarbons contained in kerosene with 5% of added n-hexane Preculturing of the biomass: a method identical to that of Example 2 was followed.

Kerosene decomposition test: 100 ml of M-culture medium containing 1 mole of sodium chloride was placed in a 500 ml ribbed neck conical flask, and after sterilization, 1 ml of a suspension of the cultured material of the DS-711 strain was inoculated thereto. After application, 10 ml of kerosene previously adjusted to a hexane concentration of 5 wt % was layered thereon, and experimentation was performed according to conditions identical to those of Example 2. The results are shown in Table 2 below.

TABLE 2

Decomposition of hydrocarbons contained in kerosene

| Hydrocarbon | Hydrocarbon amount (mg) | Control group hydrocarbons (no inoculation) | | Experimental group hydrocarbons | |
|---|---|---|---|---|---|
| | | kerosene phase | aqueous phase | kerosene phase | aqueous phase |
| n-hexane | 500.8 | 224 | ND | 210 | 0.25 |
| n-heptane | 56 | 34 | ND | ND | 0.02 |
| n-octane | 72 | 39 | ND | 11 | ND |
| n-nonane | 236 | 190 | ND | 55 | ND |
| n-decane | 312 | 245 | ND | 85 | ND |
| n-undecane | 320 | 270 | 0.04 | 96 | 0.05 |
| n-dodecane | 704 | 652 | 0.08 | 167 | 0.09 |
| n-tridecane | 596 | 501 | 0.09 | 100 | 1.7 |
| n-tetradecane | 364 | 332 | 0.09 | 45 | 1.5 |
| n-pentadecane | 212 | 188 | 0.07 | 16 | 2.3 |
| n-hexadecane | 48 | 39 | 0.02 | 9 | 0.9 |

EXAMPLE 4

Decomposition of heavy oil by means of the DS-711 strain

Preculturing: according to a method identical to that of Example 2. Heavy oil decomposition test: 100 ml of M-culture medium containing 1 mole of sodium chloride was placed in a 500 ml ribbed neck conical flask, and after sterilization, 1 ml of a suspension of the material to be cultured was placed thereon, 5 ml of C-heavy oil (produced by Idemitsu Petroleum Co., Ltd.) was layered thereon, and this was cultured while being gently agitated for a period of 2 weeks at a temperature of 28° C. After culturing, centrifugal separation was conducted, the biomass was removed, the clear upper liquid thereof was transferred to a separatory funnel, 100 ml of hexane was added, the hydrocarbons were extracted, and after the extracted liquid was dehydrated by means of magnesium sulfate, the hydrocarbons were eluted by means of silicic acid column chromatography (silicic acid/Celite=9/1, 20 g, column 25 mm×100 mm, eluting solvent: n-hexane 150 ml). The eluted liquid was vacuum concentrated by means of a rotary evaporator to a specific concentration, and the straight chain hydrocarbons having 9 to 16 carbon atoms were analyzed by means of gas chromatogrphy. The results thereof are shown in Table 3 below.

TABLE 3

Decomposition of hydrocarbons contained in heavy oil

| Hydrocarbon | Hydrocarbon amount (mg) | Control group hydrocarbons (no inoculation) | Experimental group hydrocarbons |
|---|---|---|---|
| n-nonane | 15 | 11 | 0.7 |
| n-decane | 21 | 16 | 0.8 |
| n-undecane | 25 | 22 | 1.1 |
| n-dodecane | 45 | 39 | 2.6 |
| n-tridecane | 49 | 41 | 2.4 |
| n-tetradecane | 40 | 36 | 2.2 |
| n-pentadecane | 35 | 29 | 1.9 |
| n-hexadecane | 29 | 22 | 1.2 |

No measurements were made concerning hexane, heptane, and octane.

EXAMPLE 5

Test for tolerance to salinity of the DS-711 strain

Preculturing: 10 ml of M-culture medium was placed in a large test tube, and biomass was scraped off from the stored slanted surface of the DS-711 strain by means of a platinum loop, and inoculated thereto. After inoculation, this was cultured while being shaken vigorously for one full day at a temperature of 37° C.

Tolerance to salinity test: 10 ml of M-culture medium which had been so adjusted in advance that the saline concentration thereof ranged from 0–3.5 moles as shown in Table 4 below, was placed in a large test tube, and after sterilization, 0.025 ml of the above-described suspension of the material to be cultured was inoculated thereto, and this was cultured while being vigorously agitated for a period of 5 days at a temperature of 37° C. After culturing, the growth in biomass was measured by absorbance at a wavelength of 660 nm ($O.D._{660}$). The results thereof are shown in Table 4 below.

TABLE 4

| Salinity and growth of biomass | | | | | | | |
| --- | --- | --- | --- | --- | --- | --- | --- |
| Salinity (mole) | 0 | 1.0 | 1.5 | 2.0 | 2.5 | 3.0 | 3.5 |
| Growth ($O.D._{660}$) | 1.22 | 1.34 | 1.22 | 1.02 | 1.00 | 0.99 | 0.02 |

From the above results, it can be seen that the DS-711 strain exhibits growth even at a salinity of 3.0 moles.

EXAMPLE 6

Test for tolerance to organic solvents of the DS-711 strain

Preculturing: conducted according to a method identical to that of Example 2.

Organic solvent tolerance test: 5 ml of M-culture medium containing 1 mole of sodium chloride was placed in a large test tube and sterilized.

After sterilization, 0.025 ml of a suspension of the above-described precultured material was inoculated thereto, and organic solvents were layered onto the culture medium in the varying concentration as shown in Table 5 below. After this, culturing was conducted while shaking vigorously for a period of 5 days at a temperature of 28° C. After culturing, the culture media were left to stand for 30 minutes, and an organic solvent layer and culture medium layer were separated. 0.1 ml of the culture medium layer was added to 0.9 ml of a physiological saline solution, this was diluted 10 times, and the diluted liquid thus obtained was appropriately diluted by factors of 10 utilizing an identical procedure to prepare diluted liquids from 10 to $10^6$ times. 0.1 ml of each diluted liquid was sprayed onto M-agar culture medium containing 1 mole of sodium chloride and 1.5% of agar, this was cultured for 2 days at a temperature of 37° C., the number of colonies formed after culturing was measured, this was multiplied by the dilution coefficient, the number of bacteria present in the cultured liquid was calculated, and the bacterial density corresponding to 1 ml of culture medium was determined in the form of a cell count (cells/ml). The results thereof are shown in Table 5 below.

TABLE 5

| Growth of the DS-711 strain in a culture medium to which various organic solvents had been added ($\times 10^8$ cells/ml) | | | | |
| --- | --- | --- | --- | --- |
| Concentration (v/v %) | 0 | 1 | 5 | 10 |
| hexane | 1.22 | 1.24 | 1.10 | no growth |

TABLE 5-continued

| Growth of the DS-711 strain in a culture medium to which various organic solvents had been added ($\times 10^8$ cells/ml) | | | | |
| --- | --- | --- | --- | --- |
| Concentration (v/v %) | 0 | 1 | 5 | 10 |
| benzene | | 1.35 | no growth | no growth |
| toluene | | 1.29 | 1.30 | no growth |
| xylene | | 1.32 | 1.30 | no growth |

EXAMPLE 7

Test for tolerance to an organic solvent mixture of the DS-711 strain

Preculturing: conducted in a manner identical to that of Example 2.

Tolerance test: conducted in a manner identical to that of Example 6. The organic solvent mixtures which were layered on the culture medium after the inoculation of the biomass were adjusted so as to have the density shown in the table below. The results thereof are shown in Table 6.

TABLE 6

| Growth of the DS-711 strain in a culture medium to which various mixtures of organic solvents had been added ($\times 10^8$ cells/ml) | |
| --- | --- |
| Organic solvents | Growth |
| benzene 1%, hexane 1%, toluene 1%, and xylene 1% | 1.28 |
| benzene 1%, hexane 5%, toluene 5%, and xylene 5% | 0.23 |
| benzene 1%, hexane 10%, toluene 10%, and xylene 10% | no growth |
| Solvents not added | 1.22 |

EXAMPLE 8

Pressure tolerance test of the DS-711 strain

Preculturing: conducted in a manner identical to that of Example 2. Pressure tolerance test: A silicone cap was attached to a 12 mm × 75 mm test tube and this was sterilized. 1 ml of a suspension of the abovedescribed precultured material was applied to a 50 ml of M-culture medium containing 1 mole of sodium chloride so that $O.D._{660}$ became 0.02, and this was placed in the above-described sterilized test tube in a sterile manner by means of a syringe. Next, this was placed in a titanium high-pressure cultivator (made by Rigo Corporation). The interior of the cultivator was filled with tap water, and pressurization to the pressure shown in Table 7 below was conducted by means of a pump used in the high-pressure culturing receptical. After pressurization, this was left to stand for 1 week at a temperature of 35° C. and cultured. After culturing, the growth in the biomass in the culture medium was measured at $O.D._{660}$, and the bacillus density in the culture medium was measured by means of the method explained in Example 6. The results thereof are shown in Table 7 below.

TABLE 7

| Pressure (atm) | Growth ($O.D._{660}$) | Biomass density (cells/ml) |
| --- | --- | --- |
| 1 | 0.389 (0.004) | $6 \times 10^7$ |
| 200 | 0.191 (0.005) | $2 \times 10^7$ |
| 400 | 0.022 (0.005) | $2 \times 10^6$ |

The values within the parentheses in the "Growth ($O.D._{660}$)" column indicate the case in which the biomass was not applied. Furthermore, the initial biomass density was $O.D._{660} = 0.01$ ($1 \times 10^6$ cells/ml).

EXAMPLE 9

Sulfurous acid tolerance test of the DS-711 strain

Preculturing: 10 ml of M-culture medium containing 1 mole of sodium chloride to which sulfurous acid had not been added was placed in a large test tube, and this was sterilized. After sterilization, biomass was scraped off from a stored slanted surface for the DS-711 strain using a platinum loop, and this was cultured while being vigorously shaken for a period of 1 day at a temperature of 37° C.

Sulfurous acid tolerance test: 5 ml of a double concentrated M-culture medium containing 2 moles of sodium chloride to which sulfurous acid had not been added was placed in a large test tube, and this was sterilized. Furthermore, using a previously sterilized 10% acidic solution of sodium sulfite and sterilized distilled water, mixtures were prepared in a sterile manner so that the total volume thereof was 10 ml and the sulfite concentration was as shown in Table 8 below.

After preparation, 0.025 ml of a suspension of the above-described precultured material was applied, and this was cultured while being vigorously shaken for 3 days at a temperature of 37° C. The growth of the biomass after culturing was measured at $O.D._{660}$. The results are shown in Table 8 below.

TABLE 8

| Sulfite ion (ppm) | 0 | 25 | 50 | 250 | 500 | 10000 |
|---|---|---|---|---|---|---|
| Growth ($O.D._{660}$) | 1.2 | 1.5 | 1.45 | 1.12 | 1.05 | 0.85 |

EXAMPLE 10

Separation method and properties of the hydrocarbon emulsifier and stabilizer (1) Recovery of the hydrocarbon emulsifier and solubilizer produced by the deep sea microorganism strain DS-711

The recovery of the hydrocarbon emulsifier and solubilizer was carried out in accordance with the method of Reddy, et al., (Biotechnology and Bioengineering, vol. 25, pp. 387–401, 1983).

1 L of M-culture medium was placed in a 5 L ribbed neck conical flask, and after sterilization, DS-711 strain which had been cultured in advance in 50 ml of the same culture medium was applied thereto, 1 ml of kerosene was layered thereon, and this was then cultured while being shaken for a period of 1 week at a temperature of 35° C. After culturing, centrifugal separation was carried out at 12000 rpm, the biomass was removed, and this operation was repeated 3 times. The clear upper liquid was transferred to a separatory funnel, the 950 ml remaining after the removal of the remaining kerosene of the upper layer was transferred to a 5 L conical flask, 3 L of acetone which had been refrigerated in advance was added, this was agitated and mixed, and was left standing for a period of 3 days at 4° C. After this, centrifugal separation was conducted, approximately 5 g of precipitate was recovered, this was dissolved in 100 ml of distilled water, 300 ml of acetone was added and mixed with this, this was again left standing for a period of 1 day at a temperature of 4° C., centrifugal separation was conducted, and a precipitate was recovered. The recovered precipitate was vacuum dried in a rotary evaporator, the acetone was removed, and this was stored at a temperature of 4° C.

(2) Physicochemical properties of the hydrocarbon emulsifier and solubilizer

Based on the stipulations of the "agricultural chemical experimental method", the hydrocarbon emulsifier and solubilizer obtained in (1) above was analyzed for proteins, carbohydrates, lipids, and ash.

| | |
|---|---|
| Yield | 4.9 g/l - culturing liquid |
| Color and form | Milky-white powder |
| Solubility | Exhibits some cloudiness and viscosity when dissolved in distilled water at room temperatures; precipitation of some undissolved material occurs. Insoluble in organic solvents such as toluene, ether, chloroform and the like. |
| pH | 8.7 (when suspended in distilled water) |
| Protein (Lowry) | 12.4% |
| Carbohydrates (Anthrone) | 15.9% |
| Lipids (MEK extract) | 25.9% |
| Ash | 40.7% |

50 ml of the hydrocarbon emulsifier and solubilizer adjusted to a density of 50 mg/ml was placed in a cellulose tube for dialysis, and dialysis was conducted for a period of 2 days with distilled water.

After dialysis, the hydrocarbon emulsifier and solubilizer exhibited the following analytical values.

| | |
|---|---|
| pH | 7.2 (when suspended in distilled water) |
| Protein | 18.4% |
| Carbohydrates | 14.8% |
| Lipids | 28.6% |
| Ash | 0.9% |

EXAMPLE 11

Production of the hydrocarbon emulsifier and solubilizer

1 L of M-culture medium adjusted to a saline concentration of 1 mole was placed in a 3 L ribbed neck conical flask, and after sterilization, a biomass of the DS-711 strain was taken from a stored slanted surface and added. After this was added, culturing was conducted under the various culturing conditions shown in Tables 9 to 12 below, and after culturing, the hydrocarbon emulsifier and solubilizer was extracted according to the methods shown in Example 10.

(1) Relationship between culture medium and pH yield

TABLE 9

| pH | Yield (g/L) |
|---|---|
| 5.0 | 3.5 |
| 6.0 | 4.7 |
| 7.0 | 4.9 |
| 8.0 | 4.9 |
| 9.0 | 4.5 |

Culturing temperature: 35° C., culturing period: 5 days, saline density: 1 mol (2) Relationship between culturing temperature and yield

TABLE 10

| Temperature (°C.) | Yield (g/L) |
|---|---|
| 25 | 4.5 |
| 30 | 4.9 |

TABLE 10-continued

| Temperature (°C.) | Yield (g/L) |
|---|---|
| 35 | 4.9 |
| 40 | 4.0 |

Initial pH of the culture medium: 7.0, saline density: 1 mol, culturing period: 5 days (3) Relationship between saline density and yield

TABLE 11

| Salt (M) | Yield (g/L) |
|---|---|
| 0 | 4.1 |
| 0.2 | 4.7 |
| 0.5 | 4.9 |
| 1.0 | 4.9 |
| 1.5 | 4.8 |
| 2.0 | 4.4 |
| 3.0 | 2.7 |
| 3.5 | 0.2 |

Culturing temperature: 35° C., culturing period: 5 days, pH of the culture medium: 7.0

(4) Relationship between culturing period and yield

TABLE 12

| Period (days) | Yield (g/L) |
|---|---|
| 1 | 4.7 |
| 2 | 4.9 |
| 3 | 4.9 |

Culturing temperature: 35° C., pH of the culture medium: 7.0, saline density: 1 mol

EXAMPLE 12

Emulsification testing of the hydrocarbon emulsifier and solubilizer

The hydrocarbon emulsifier and solubilizer obtained in Example 10 was dissolved in distilled water and sea water so as to be present in a concentration of 10 mg/ml, 0.5 ml of kerosene, heavy oil, or other hydrocarbons were layered on to 50 ml of each solution, this was the vigorously agitated for 30 minutes at room temperature, allowed to stand for 30 minutes, and the turbidity of the water layer was measured by a photometer (wavelength 660 nm). The results thereof are shown in Table 13 below.

TABLE 13

| | Control group | | Experimental group | |
|---|---|---|---|---|
| | Sea water | Distilled water | Sea water | Distilled water |
| Kerosene | 0.004 | 0.007 | 0.041 | 0.188 |
| Heavy oil | 0.002 | 0.008 | 0.133 | 0.442 |
| n-octane | 0.002 | 0.007 | 0.087 | 0.224 |
| n-nonane | 0.005 | 0.009 | 0.109 | 0.186 |
| n-decane | 0.003 | 0.008 | 0.067 | 0.243 |
| n-undecane | 0.004 | 0.008 | 0.075 | 0.165 |
| n-dodecane | 0.002 | 0.008 | 0.065 | 0.223 |
| n-tridecane | 0.002 | 0.007 | 0.082 | 0.158 |
| n-tetradecane | 0.004 | 0.008 | 0.092 | 0.262 |
| n-pentadecane | 0.004 | 0.009 | 0.071 | 0.211 |
| n-hexadecane | 0.005 | 0.008 | 0.097 | 0.233 |

EXAMPLE 13

Solubilization testing of the hydrocarbon emulsifier and solubilizer

The hydrocarbon emulsifier and solubilizer obtained in Example 10 was dissolved in distilled water and sea water so as to be present at a concentration of 10 mg/ml, 0.5 ml of kerosene or other hydrocarbons was layered on 50 ml of each of these solutions, this was vigorously stirred for a period of 30 minutes at room temperature, and after stirring, these solutions were placed in a separatory funnel and left standing for a period of 30 minutes, thus separating the oil layer and the water layer. 40 ml of the lower layer was taken and filtered through a 0.45 micron membrane filter, 50 ml of benzene containing as a internal standard 0.1 g of eicosane or octacosane was added, this was vigorously agitated, and the solubilized hydrocarbons were extracted. After extraction, dehydration was carried out using sodium sulfate anhydride, and after concentration, the density of the hydrocarbons was measured using gas chromatography. The results thereof are shown in Table 14 below.

Analysis conditions of the gas chromatography: Shimadzu GC-14A, detector: single flame ionization detector, column: glass column (2.1 m×3.2 m/m), carrier: silicone 10% OV-101 60/80 mesh chromosorb W AW-DMCS, carrier gas: $N_2$ (40–50 ml/min), temperature: 35°–300° C. (programmed speed 10° C./min).

TABLE 14

| | Hydrocarbons dissolved in the water layer | | | |
|---|---|---|---|---|
| | Control group | | Experimental group | |
| Hydrocarbons | Sea water | Distilled water | Sea water | Distilled water |
| alkanes in kerosene | | | | |
| n-nonane | 0.008 | 0.006 | 0.8 | 1.2 |
| n-decane | 0.018 | 0.018 | 1.9 | 2.1 |
| n-undecane | 0.017 | 0.019 | 2.2 | 2.6 |
| n-dodecane | 0.015 | 0.016 | 2.9 | 3.5 |
| n-tridecane | 0.013 | 0.014 | 2.7 | 4.4 |
| n-tetradecane | 0.011 | 0.012 | 1.8 | 2.9 |
| n-pentadecane | 0.012 | 0.014 | 1.1 | 2.6 |
| n-hexadecane | 0.011 | 0.013 | 0.9 | 1.2 |
| individual alkanes | | | | |
| n-decane | 0.02 | 0.02 | 0.9 | 2.2 |
| n-undecane | 0.05 | 0.04 | 1.3 | 5.2 |
| n-dodecane | 0.06 | 0.07 | 3.3 | 12.0 |
| n-tridecane | 0.05 | 0.09 | 7.3 | 33.7 |
| n-tetradecane | 0.09 | 0.07 | 5.3 | 15.6 |
| n-pentadecane | 0.04 | 0.08 | 5.2 | 14.9 |
| n-hexadecane | 0.03 | 0.05 | 4.2 | 7.3 |

Hydrocarbons having from 6 to 8 carbon atoms which are contained in the kerosene are not detectable by means of gas chromatography.

EXAMPLE 14

Heavy oil viscosity test

The viscosity of C-heavy oil was measured at the temperatures shown in the table below using a Cannon-Fenski tube type kinetic viscosity meter (made by Shibata Scientific Machine Industries Co.: Viscometers Nos. 500 and 600) in accordance with the method of JIS K2283. The sample used for measurement was prepared in the following manner.

100 g of C-heavy oil produced by Idemitsu Petroleum Co., Ltd. was placed in a 200 ml glass beaker, 1 ml of the emulsifier and solubilizer of the present invention dissolved in distilled water so as to be present in a concentration of 50 mg/ml was added thereto, and this was sufficiently agitated and mixed. Furthermore, for the purposes of reference, heavy oil to which 1 ml of distilled water had been added was used. The results thereof are shown in Table 15.

TABLE 15

| Temperature (°C.) | Viscosity (cSt) | |
|---|---|---|
| | Control group | Experimental group |
| 10 | more than 20000 | 16800 |
| 25 | 12200 | 6363 |
| 50 | 8484 | 2333 |

Viscosity meter coefficient C = 7.07 (No. 500)
C = 20 (No. 600)

The viscosity of the heavy oil was reduced when heated; however, when comparing the case in which the emulsifier and solubilizer of the present invention was added with the case in which it was not added, it is clear that the drop in viscosity is striking. That is to say, the hydrocarbon emulsifier and solubilizer of the present invention possesses the ability to reduce heavy oil viscosity. For this reason, it is possible to use the hydrocarbon emulsifier and solubilizer of the present invention as a cleaning agent for heavy oil tanks, a viscosity reducing agent for bottom sludge, and the like.

EXAMPLE 15

Separation of an organic-solvent tolerant microorganism:

1 g of a sample was placed in a test tube, 5 ml of distilled water or artificial sea water (both having a pH of 6) was added thereto, this was sufficiently agitated, and the sample was dispersed. Organic solvent was added thereto so as to raise the total volume to 10 ml, a silicone rubber cap was applied, and shaking culturing was conducted for a period of 7 days at a temperature of 10° C. During this period of time, microorganisms which were capable of surviving or growing in the organic solvent moved to the organic solvent phase. After the completion of culturing, the cultured material was placed in a separatory funnel, this was left to stand for 1 hour, and the water phase and the organic solvent phase were separated. 100 microliters of the organic solvent phase was obtained, this was sprayed onto an agar culture medium, culturing was conducted for a period of 7 days at a temperature of 30° C., and the microorganisms which grew therein were isolated.

Composition of the artificial sea water

This contained 3% of sodium chloride, 0.1% of calcium chloride, 0.1% of magnesium chloride, and 0.1% of potassium chloride.

Composition of the agar culture medium

The agar culture medium contained 0.5% of proteose peptone, 0.25% of phytone peptone, 0.1% of calcium chloride, 0.01% of magnesium chloride, 5.8% of sodium chloride, 50 ppm of sodium sulfite, and 2% of agar. An agar culture medium containing 0.5% of yeast extract, 1% of tryptone, 0.5% of sodium chloride, and 2% of agar may also be used, and where necessary, 0.1% of calcium chloride and 0.01% of magnesium chloride may be added thereto.

Composition of the liquid culture medium

Identical to the above, with the exception that agar was not included therein.

Evaluation of the organic-solvent tolerant microorganism 5 ml of the liquid culture medium was placed in a test tube, and this was sterilized for a period of 20 minutes in an autoclave at a temperature of 120° C. using a platinum wire loop, the isolated microorganisms were applied to a culture medium, shaking culturing was conducted for 1 day at a temperature of 35° C., and a suspension of precultured microorganisms was prepared. 5 ml of liquid culture medium was placed in a test tube, and sterilization was carried out in accordance with the above conditions. 100 microliters of the suspension of microorganisms was applied to the sterilized culture medium, a further 50 microliters of organic solvent was added thereto, a silicone rubber cap was applied, and agitation culturing was conducted at a temperature of 30° C. After the completion of agitation, microorganisms for which an increase in the absorbancy of the culture medium at a wavelength of 660 nm could be recognized, in comparison with a control to which microorganisms had not been added, were judged to be organic-solvent tolerant microorganisms.

The results thereof are shown in Table 16. As a result of considering the separation sources, it was determined that organic-solvent tolerant microorganisms could be efficiently separated by the method of the present invention irrespective of separation sources.

TABLE 16

Numbers of organic-solvent tolerant microorganisms separated from 1 g of various samples

| Sample | Soil sample | | | | Deep-sea sample | | | | | |
|---|---|---|---|---|---|---|---|---|---|---|
| | A | B | C | D | E | F | G | H | I | J |
| Number of strains | 10 | 7 | 11 | 16 | 19 | 37 | 48 | 52 | 9 | 4 |

A, B, C, and D represent soil samples obtained randomly from various locations by the Institute of Physical and Chemical Research.

E, F, and G represent silt samples obtained from the floor of Suruga Bay.

H, I, and J represent silt samples obtained from the floor of Sagami Bay.

Distilled water was used for the water phase in samples A to D, while artificial sea water was used in the water phase of E to J.

The microorganism separated from sample G in these examples, that is to say, the microorganism separated from ocean floor silt from the bottom of Suruga Bay at a depth of 1945 m, is a novel microorganism, and was designated as the DS-711 strain belonging to the genus Flavobacterium.

EXAMPLE 16

Using sample G, and conforming to the conditions of Example 15, the ratio of organic solvent phase and water phase (artificial sea water) was altered as shown in Table 17 below, and the number of organic-solvent tolerant microorganisms which were separated was determined.

The results thereof are shown in Table 17. Efficient separation was achieved at a volumetric ratio of 5:5, however, it was determined that organic-solvent tolerant microorganisms could be obtained even at other volumetric ratios.

TABLE 17

Relationship between organic solvent/water ratio and the number of organic-solvent resistant microorganisms separated

| Organic solvent | Organic solvent/Water (V/V) | Number of organic-solvent tolerant microorganisms separated/Sample (1 g) |
|---|---|---|
| benzene | 1:9 | 17 |

TABLE 17-continued

Relationship between organic solvent/water ratio and the number of organic-solvent resistant microorganisms separated

| Organic solvent | Organic solvent/Water (V/V) | Number of organic-solvent tolerant microorganisms separated/Sample (1 g) |
| --- | --- | --- |
|  | 3:7 | 29 |
|  | 5:5 | 48 |
|  | 7:3 | 32 |
|  | 9:1 | 41 |
| toluene | 5:5 | 79 |
| xylene | 5:5 | 98 |

EXAMPLE 17

Using benzene as the organic solvent, and setting the benzene:water (artificial sea water) ratio at 5:5, and proceeding in the manner of Example 15, with the exception that the culturing period was altered as shown in Table 18 below, the number of organic-solvent tolerant microorganisms which were separated was determined.

The results thereof are shown in Table 18 below. A period of 7 days is desirable as the culturing period; however, it was determined that a large number of the organic-solvent tolerant microorganisms which are an object of the present invention could be obtained with a culturing period as short as 1 day.

TABLE 18

Relationship between culturing period and the number of organic-solvent tolerant microogranisms which were separated

| Culturing period (days) | Number of organic-solvent tolerant microorganisms separated from 1 g of the sample | |
| --- | --- | --- |
|  | SAMPLE F | SAMPLE G |
| 1 | 21 | 30 |
| 2 | 26 | 32 |
| 5 | 27 | 39 |
| 7 | 37 | 48 |

EXAMPLE 18

Using benzene as the organic solvent and setting the benzene:water (artificial sea water) ratio at 5:5, and proceeding in a manner identical to that of Example 15, with the exception that the culturing temperatures were altered as shown in Table 19 below, the number of organic-solvent tolerant microorganisms which were separated was determined.

The results thereof are shown in Table 19. In the case of all the examples, the largest number of organic-solvent tolerant microorganisms was obtained when culturing was conducted at a temperature of 10° C.; however, organic-solvent tolerant microorganisms could be efficiently obtained by means of culturing within a temperature range of 4°–30° C.

TABLE 19

Relationship between culturing temperature and number of organic-solvent tolerant microorganisms which were separated

| Culturing temperature (°C.) | Number of organic-solvent tolerant microorganisms separated from 1 g of the sample | |
| --- | --- | --- |
|  | SAMPLE F | SAMPLE G |
| 4 | 31 | 34 |
| 10 | 37 | 48 |
| 20 | 28 | 29 |
| 30 | 26 | 28 |

EXAMPLE 19

Using benzene as the organic solvent, and setting the benzene:water (artificial sea water) ratio to 5:5, using sample G, and proceeding a manner identical to that in Example 1, with the exception that the pH of the water phase was altered as shown in Table 20, the number of organic-solvent tolerant microorganisms which were separated was determined. The adjustment of the pH was conducted by means of sodium hydroxide and sulfuric acid. The results thereof are shown in Table 20.

Organic-solvent tolerant microorganisms could be efficiently obtained when the pH of the sample suspended in the water phase was within a range of from 5 to 8. In contrast, under acidic conditions in which the water phase pH was 3 and under alkali conditions in which the water phase pH was 10, the number of organic-solvent tolerant microorganisms obtained decreased sharply. Accordingly, the pH of the water phase used for processing should preferably be close to neutral.

TABLE 20

Relationship between water phase pH and the number of organic-solvent tolerant microorganisms separated

| Water phase pH | Number of organic-solvent tolerant microorganisms separated from 1 g of the sample | |
| --- | --- | --- |
|  | SAMPLE F | SAMPLE G |
| (Case in which distilled water was used) | | |
| 3 | 2 | 7 |
| 5 | 14 | 19 |
| 6 | 15 | 19 |
| 7 | 12 | 20 |
| 8 | 10 | 18 |
| 10 | 0 | 2 |
| (Case in which artificial sea-water was used) | | |
| 3 | 4 | 8 |
| 5 | 29 | 41 |
| 6 | 37 | 48 |
| 7 | 33 | 39 |
| 8 | 30 | 38 |
| 10 | 3 | 9 |

The novel microorganism of the present invention exhibits superior decomposition activity with respect to hydrocarbons. Furthermore, the microorganism possesses tolerance to sulfurous acids, salinity, and various organic solvents, including hexane, which are in general toxic with respect to microorganisms, so that it is capable of effectively decomposing oil pollution products such as heavy oil floating at sea. Furthermore, the microorganism is not limited to the decomposition of oil products at sea, but rather may be used in a variety of environments in order to decompose various solvents.

The hydrocarbon emulsifier and solubilizer produced by the DS-711 strain of the present invention is capable of effectively emulsifying and solubilizing hydrocarbons, and maintains this ability even in sea water. Accordingly, the hydrocarbon emulsifier and solubilizer of the present invention is capable of effectively emulsifying and solubilizing polluting oil products such as kerosene, heavy oil, or the like, floating at sea. Furthermore, the use thereof is not limited to the emulsification or solubilization of oil products at sea; rather, it is capable of effectively emulsifying and solubilizing various polluting organic solvents in various other environments.

In accordance with the present invention, it is possible to efficiently separate a microorganism which has superior tolerance to organic solvents from a sample in a short period of time.

What we claim is:

1. A biologically pure culture of a microorganism belonging to the genus Flavobacterium, designated FERM BP-4010 having the ability to decompose hydrocarbons and having tolerance to salinity, organic solvents, sulfurous acids and pressure.

2. A biologically pure culture of a mutant strain derived from Flavobacterium strain FERM BP-4010 possessing all of the identifying characteristics of said parent strain having the ability to decompose hydrocarbons and having tolerance to salinity, organic solvents, sulfurous acids and pressure.

* * * * *